United States Patent [19]

Kolehmainen et al.

[11] 4,264,727

[45] Apr. 28, 1981

[54] ASSAYING OF DIGOXIN BY MEANS OF BIOLUMINESCENCE AND INHIBITION OF NA+ - K+-ATPASE

[76] Inventors: Seppo Kolehmainen, Ganzenstraat 11, 3540 Zolder, Belgium; Veikko Tarrkkanen, Breulsweg, Wylre 1, Netherlands

[21] Appl. No.: 60,006

[22] Filed: Jul. 24, 1979

[30] Foreign Application Priority Data

Jul. 26, 1978 [GB] United Kingdom ............... 31144/78

[51] Int. Cl.$^3$ .............................................. C12Q 1/66
[52] U.S. Cl. .......................................... 435/8; 435/21
[58] Field of Search ................................. 435/8, 18, 21

[56] References Cited

U.S. PATENT DOCUMENTS

| 3,769,414 | 10/1973 | Brooker | 435/21 X |
| 4,039,385 | 8/1977 | Ullman et al. | 435/21 X |
| 4,080,265 | 3/1978 | Antonik | 435/8 |
| 4,104,029 | 8/1978 | Maier | 435/8 X |
| 4,104,126 | 8/1978 | Young | 435/8 X |

Primary Examiner—Thomas G. Wyse

[57] ABSTRACT

A method is described for quantitative measurement of digoxin and other digitaloids in serum. The method is based on the inhibition of Na+, K+—specific ATPase enzyme by digitaloids as a result of receptor binding principle and the measurement of this inhibition with the firefly luceferin—luciferase bioluminescence assay of APT. Method is specific and has similar sensitivity to that of the commonly used radioimmunoassay, but simpler and can be performed with low-cost instrumentation.

3 Claims, No Drawings

ASSAYING OF DIGOXIN BY MEANS OF BIOLUMINESCENCE AND INHIBITION OF NA+-K+-ATPASE

The invention relates to a new method for measuring digoxin in serum.

Digoxin is a derivative of digitaloids and commonly used for treating patients with heart condition. The action of digoxin and other digitaloids, such as drugs obtained from *Digitalis vulgaris* plant, inhibit the activity of sodium-potassium specific ATPase enzyme. This ATPase enzyme operates the so called sodium-potassium pump that controls the cell wall permeability of muscle cells and takes part to the constriction of muscle fibres. In the wall of blood vessels there are smooth muscles that are operated by the ATPase. The effect of digitaloid drugs is supposed to be based on the reversible inactivation of sodium-potassium specific ATPase. The inhibition of this enzyme reduces the constriction of the Coronary artery and thus decreasing the possibility of blockage of this vital artery supplying oxygen rich blood to the heart muscle by tromboembolism.

Digoxin is presently a most commonly applied drug to prevent thrombosis. This drug is a cardiac glycoside. It has to be applied in narrowly controlled dosage as its mirror is narrow, that is the minimum effective treatment concentration and the toxic concentration, are close to each other. Effective treatment level varies from 0.4–2 $ng/cm^3$ and concentration over 2 ng are toxic.

The concentration of digoxin in patient's serum is presently measured by so called enzyme immunoassay. Two principles of measurement are utilized in the immunoassay: measurement of radioactive tracer in so called radioimmunoassay (RIA) and measurement of enzyme activity on so called enzyme immunoassay (EIA). In these techniques a specific antibody, produced in the blood of a test animal such as rabbit or sheep, is labeled either by a radioisotope, such as iodine—125 ($^{125}I$) or tritium ($^3H$) in RIA or with an enzyme, such as phosphatase, dehydrogenase, peroxidase which can produce a substrate forming a coloured complex with a chromogen reagents. The principles of immunoassay are known per se and they operate as following:

I.
a. Patient's serum containing digoxin (antigen) is mixed with the labeled antibody and incubated for 2–24 hrs, during which time the angiten (digoxin) in serum form a complex with the added antibody.
b. Free antibody which is not complexed with digoxin is separated by e.g. dextran-coated activated charcoal or the antigen-antibody complex is precipitated with e.g. polyethylene glycol.
c. Free labeled antibody or the labeled antibody in the complex is measured giving the concentration of digoxin in the sample. Radioactively labeled antibody is measured with gamma counter for $^{125}I$ or with liquid scintillation counter for $^3H$ and enzyme labeled antibody is measured with spectrophotometer or estimated visually from the colour intensity of the formed substratechromogen.

II. Competitive binding assay
a. Antibody is fixed on a solid surface, such as plastic cuvettes or microtiter plates.
b. Sample serum with digoxin is placed in the container having the fixed antibody. Digoxin reacts with antibody during 2–24 hrs incubation forming a complex and part of the antibody molecules are left over because they are in excess.
c. Supernatant is discarded and sample container is washed.
d. Labeled antigen (digoxin) is added, and during 2–24 hrs incubation the labeled antibody reacts with the antibody not bound with digoxin from the sample during the first incubation.
e. Supernatant is discarded and sample container is washed.
f. Labeled antigen is measured and the value gives the quantity of labeled digoxin bound during the second incubation. Digoxin in the original sample is: sample digoxin = Antibody molecules − labeled digoxin molecules.

III. Sandwich method
a. Sampler container (plastic) is fixed with antibody.
b. Sample serum is added and incubated for 2–24 hrs.
c. Supernatant is discarded and container washed, digoxin antibody complex and fixed antibody are retained in the container.
d. Labeled antibody is added and during 2–24 hrs incubation this antibody attaches on the digoxin in the first antibody-digoxin complex.
e. Supernatant is discarded to eliminate free (uncomplexed) labeled antibody. Container is washed.
f. Labeled antibody is measured giving the quantity of digoxin in the sample.

In each method a calibration curve is made with graded quantities of digoxin is serum. From this calibration curve the concentration of digoxin in serum is calculated.

Immunoassay techniques have the advantage being sensitive and specific when pure antigen and antibody reagents are used. However, these techniques are expensive, complicated and time-consuming due to long incubations. A further difficulty related to RIA is the necessity of using radioactive tracers which require a special licence for using and always pose a safety hazard and problems in disposal of radioactive waste. Chromogen method has a marginal sensitivity for digoxin test.

It is the object of the invention to overcome these difficulties of immunoassay techniques by developing a new method for measuring digoxin in serum.

According to the invention the concentration of digoxin and other digitaloids is measured with its inhibition on purified $Na^+$, $K^+$-specific ATPase enzyme.

The method according to the invention is based on the utilization of sodium-potassium specific ATPase (adenosine triphosphatease) as receptor for digoxin. Digoxin inactivates this enzyme, thus it is possible to add a known quantity of ATPase into the sample serum and measure the inhibition on the enzyme activity after a short incubation time. The measurement of ATPase activity is performed by means of the rate that ATPase breaks down added ATP (adenosine triphosphate). The ATP concentration after a short incubation time with ATPase is measured with the sensitive and specific firefly system. Luciferin-luciferase system is known per se (see U.S. Pat. No. 3,745,090).

Sodium-potassium specific ATPase is an enzyme that reacts with adenosine triphosphate (ATP), producing adenosine diphosphate (ADP) and inorganic phosphate (P) in the presence of sodium and potassium ions:

$$\text{ATP} \xrightarrow{\text{Na}^+, \text{K}^+ \text{ATPase}} \text{ADP} + \text{P}$$

Digitaloids, such as digoxin attach themselves in the Na+, K+-ATPase with a receptor principle (T. Akera, Science 198: 569–574, 1977). ATPase is the receptor attaching digoxin on a saturable binding site and the enzyme molecule having digoxin cannot react with ATP and hydrolyse it. When ATPase and digoxin are present, digoxin molecule binds to ATPase molecule and the inactivation of ATPase is directly correlated to the number of digoxin molecules present.

ATPase activity can be measured by incubating the enzyme in presence of known concentration of ATP and measuring the quantity of ATP hydrolyzed by the enzyme per unit time. The most sensitive and specific method of measuring ATP is the firefly bioluminescent system. By adding a known quantity of ATP, incubating to allow ATPase react with ATP and measuring remaining ATP with the firefly bioluminescent system, the invention presents a simple, rapid and sensitive method for measuring digoxin in sample, based on the incubation of Na+, K+-ATPase.

To carry out the method according to the invention 10-1000μl, but preferably 100μl digoxin sample is pipetted to duplicate cuvettes.

Then 0.1-50 μU, but preferably 1 μU Na+, K+-ATPase in 10 μl in a buffer such as tris (Tris-hydroxymethyl-aminomethane 0.025-0.5 M pH 7.4-7.8) and 130 mM Na+, 20 mM K+, 3 mM Mg++ for the sample volume is added and mixed. Thereafter incubation is carried out for 30-120 minutes at 37° C.

10-1000 g, but preferably 50-100 picogrammes (pg) ATP is pipetted in 1-1000 μl, but preferably 10 μl, whereafter is mixed.

The sample is incubated 1-60 minutes, but preferable 20 minutes at room temperature.

The cuvette is placed in a luminescent photometer and the produced light intensity after injection of luciferin-luciferase reagent in 10-1000 μl, but preferably 100 μl, is measured.

A calibration curve is prepared by treating a set of standard digoxin samples following the aforesaid measuring steps.

The sensitivity of the method is enough for digoxin levels between 0.2-5 ng:cm$^3$. In serum there can be enzymes that break down ATP, thus the serum has to be heated to 65° C. for 0.5-10 minutes to destroy the enzyme activity of phosphatase, kinase and possible ATPase enzymes prior to adding Na+, K+-ATPase.

We claim:

1. A method for measuring the concentration of digoxin and other digitaloids in a sample containing the same by detecting the deactivation thereof on a Na+, K+-specific ATPase enzyme, comprising:

incubating said sample, together with a quantity of Na+, K+-specific ATPase enzyme under conditions and for a period sufficient to deactivate a part of said quantity;

further incubating the resulting product with a quantity of ATP in excess of that sufficient to be hydrolyzed by said ATPase enzyme and under conditions to promote hydrolysis thereof; and measuring the resulting concentration of ATP by means of the firefly luciferin-luciferase bioluminescent reaction and quantifying such measurement to determine the concentration of digoxin and other disitaloids in the sample.

2. A method according to claim 1, wherein the activity of the ATPase enzyme is measured kinetically as a continuous declining light intensity of the bioluminescent reaction while the ATPase enzyme hydrolyzes added ATP during the measurement.

3. A method according to claim 1, wherein the measured concentration of ATPase enzyme is used to calculate the concentration of digitaloids in the sample by comparing the deactivation of Na+, K+-specific ATPase in the sample to a standard sample containing a known concentration of digitaloids.

* * * * *